United States Patent [19]

Mano et al.

[11] Patent Number: 5,998,467
[45] Date of Patent: *Dec. 7, 1999

[54] MEDICINE FOR OCULOPATHY

[75] Inventors: Tomiya Mano; Shunji Sogo, both of Osaka, Japan

[73] Assignee: Mitsubishi Chemical Corporation, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/735,241

[22] Filed: Oct. 22, 1996

[30] Foreign Application Priority Data

Oct. 25, 1995 [JP] Japan .................................. 7-278119
Mar. 29, 1996 [JP] Japan .................................. 8-075824

[51] Int. Cl.$^6$ .................................................. A61K 31/335
[52] U.S. Cl. ........................... 514/452; 514/450; 514/913
[58] Field of Search ........................... 514/450, 452, 514/913

[56] References Cited

U.S. PATENT DOCUMENTS

| | | | |
|---|---|---|---|
| 4,684,739 | 8/1987 | Kikumoto et al. | 549/350 |
| 5,169,099 | 12/1992 | Iwata et al. | 514/452 |
| 5,296,477 | 3/1994 | Taverne et al. | 514/224.2 |
| 5,652,272 | 7/1997 | Ogawa et al. | 514/652 |

FOREIGN PATENT DOCUMENTS 0 446 921  9/1991  European Pat. Off. .

OTHER PUBLICATIONS

Peroytka et al., *Neuropharmacology*, vol. 26, No. 2/3, pp. 139–146(1987).
Mano et al., *Investigative Ophthalmology & Visual Science*, vol. 37 (3) 1996 S1103 XP 000672609.

*Primary Examiner*—Zohreh Fay
*Attorney, Agent, or Firm*—Wenderoth, Lind & Ponack, L.L.P.

[57] ABSTRACT

This invention is aimed at providing a novel medicine for oculopathy, which has as an active component thereof a 5-HT$_{1A}$ receptor ligand such as, for example, an alkylene dioxybenzene derivative represented by the following formula (I)

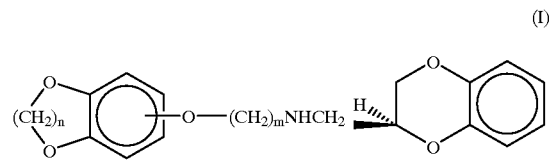

(I)

wherein m represents an integer in the range of 2–5 and n an integer in the range of 1–3), a racemate thereof, or an acid addition salt thereof.

4 Claims, 3 Drawing Sheets

MEDICINE FOR OCULOPATHY

BACKGROUND OF THE INVENTION

1. Field of the Invention

This invention relates to a medicine for oculopathy, and more particularly to medicines for oculopathy such as, for example, a therapeutic reagent for glaucoma and an intraocular pressure depressant which have a serotonin receptor 1A ligand of a specific structure as an active component.

Oculopathy like glaucoma, has been attracting growing social attention as one of the adult diseases particularly in such advanced countries as are on the verge of qualifying as a community of extremely high senility.

2. Description of the Prior Art

Oculopathy such as, for example, glaucoma refers to the group of diseases in which morbid alterations inducive of abnormal intraocular pressure injure intraocular tissues and optic nerve function in particular. As concerns the mechanism which is responsible for the morbid alterations, it is generally held that the morbid alterations are mainly caused by the symptom of ischemia and the disturbed blood flow in the axial cylinder of the optic nerve owing to the disturbance of circulation in the optic nerve disc which originates in the elevation of the intraocular pressure. Various medicinal therapies aimed at the adjustment of the intraocular pressure have been tried with success (as reported in "Ophthalmology Mook No. 9, 1979, 'Therapy of Glaucoma,' published by Kanahara Publishing Co., Ltd.," for example). The mechanism responsible for the elevation of the intraocular pressure, however, remains yet to be elucidated and the desirability of developing a better medicine for the therapy of glaucoma has been finding enthusiastic recognition.

The ligand of the serotonin receptor is known to manifest various pharmacological actions such as the action to contract the blood vessels, the action to stimulate the sympathetic nervous system, anti-depression activity, the action to decrease blood pressure, and anti-platelet aggregation activity and has been used for the therapy of diseases as an agent for anti-depression, an agent for anti-anxiety, and an agent for anti-hypertension. Among the serotonin receptor ligands, an alkylene dioxybenzene derivative is a selective ligand of the serotonin receptor 1A (hereinafter occasionally referred to briefly as "5-HT$_{1A}$ receptor") and is known to have the action to decrease blood pressure and anti-anxiety activity (U.S. Pat. No. 4,684,739 and U.S. Pat. No. 5,168,099).

SUMMARY OF THE INVENTION

This invention has been produced for the purpose of providing a more effective medicine for oculopathy such as, for example, an agent for the cure of glaucoma and an agent for lowering the intraocular pressure.

The present inventors, after continuing a diligent study with a view to solving the problems incurred by the prior art as described above, have found that the serotonin receptor 1A ligand such as, for example, an alkylene dioxybenzene derivative of a specific structure possesses an excellent action to lower the intraocular pressure and can serve as a medicine for the cure of oculopathy such as glaucoma. The present invention has been perfected as a result.

Specifically, this invention provides a medicine for oculopathy which has a serotonin receptor 1A (5-HT$_{1A}$ receptor) ligand as an active component thereof.

Preferred embodiments of this invention provide the medicine mentioned above, the 5-HT$_{1A}$ receptor ligand of which is an alkylene dioxybenzene derivative represented by the following formula (I)

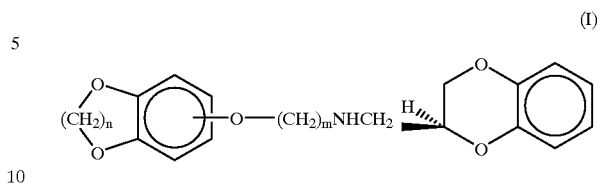

(I)

(wherein m represents an integer in the range of 2–5 and n represents an integer in the range of 1–3), a racemate thereof, or an acid addition salt thereof; the medicine mentioned above the alkylene dioxybenzene derivative of which is a compound represented by the following formula (II)

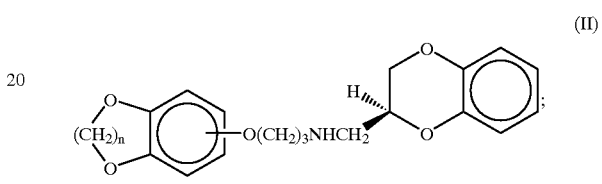

(II)

the medicine for oculopathy mentioned above as an agent for the cure of glaucoma; the medicine for oculopathy mentioned above as an agent for lowering the intraocular pressure; the medicine for oculopathy mentioned above as an oral agent; the medicine for oculopathy mentioned above as an agent used by injection; and the medicine for oculopathy mentioned above as an eye lotion.

DETAILED DESCRIPTION OF THE INVENTION

Figure 1:
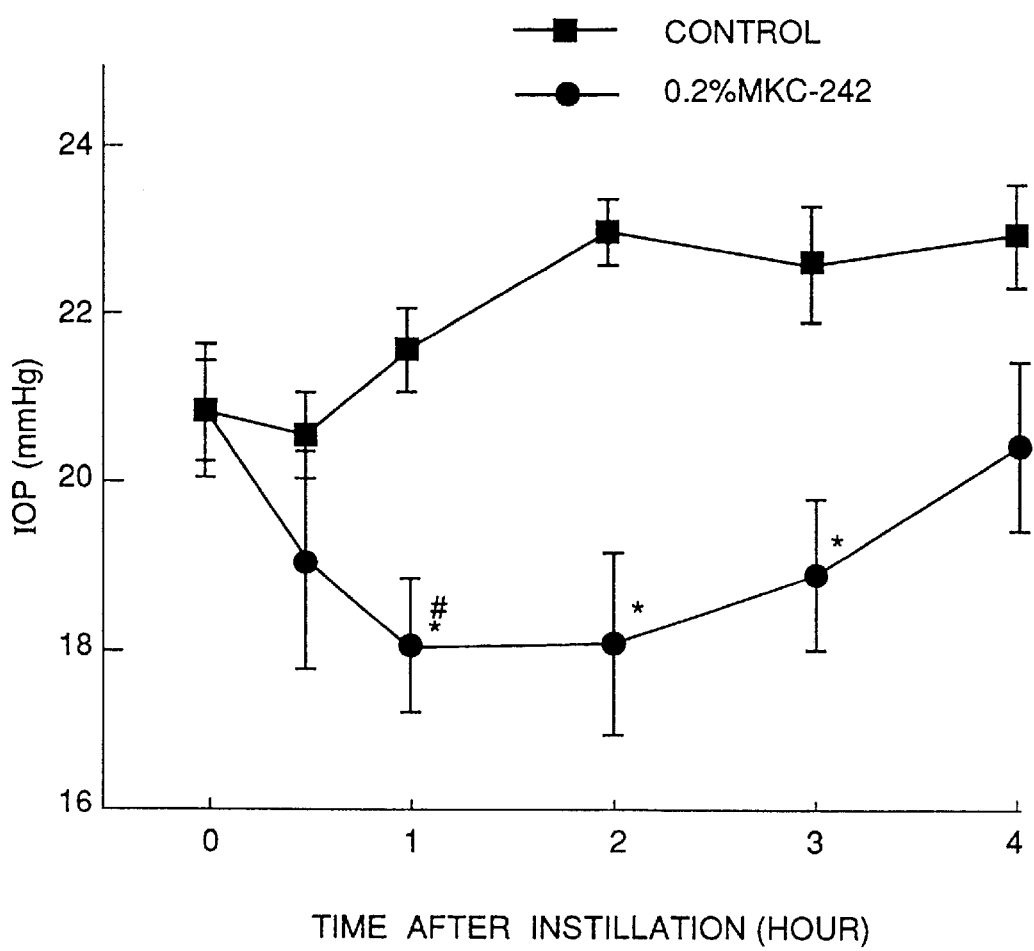
FIG. 1 is a diagram illustrating the action to lower the intraocular pressure manifested by MKC-242 applied dropwise to the eye. In the diagram, the points of measurement and the bars represent the average +/−S.E. of the intraocular pressures in 8 rabbits; # represents the significant difference ($P<0.01$) from the initial intraocular pressure; and * represents the significant difference ($P<0.01$) from the intraocular pressure of the control group.

This invention will be described below with reference to embodiments thereof.

The 5-HT$_{1A}$ receptor ligand which is used as the effective component of the medicine of this invention for oculopathy may be any compound which satisfies the requirement that it is bound specifically with the 5-HT$_{1A}$ receptor and posses of an action to lower intraocular pressure. As concrete examples of the compound answering this description, 8-hydroxy-2-(N,N-dipropylamino)-tetralin (hereinafter occasionally referred to as "8-OH-DPAT"), 2-(4-(4-(2-pyrimidinyl)-1-piperazinyl)butyl)-1,2-benzisothiazol-3-(2H)on-1,1-dioxydehydrochloride (hereinafter occasionally referred to as "TVX Q 7821") which are described in "Neuropharmacology, Vol. 26, No. 2/3, pp. 139–146 (1987)," for example; and alkylene dioxybenzene derivatives represented by the formula (I) mentioned above, racemates thereof, and acid addition salts thereof, and arbitrary hydrates thereof may be cited. Among other 5-HT$_{1A}$ receptor ligands enumerated above, the compounds represented by the formula (I) mentioned above, racemates thereof, and acid addition salts thereof, and arbitrary hydrates thereof prove particularly advantageous.

Among the alkylene dioxybenzene derivatives of the formula (I) mentioned above which have the integers of 2–5 for m and the integers of 1–3 for n, the compounds having the integer of 3 or 4 for m and the integers of 1–3 for n prove more advantageous and those having the integer of 3 for m and the integer of 1 for n prove most advantageous.

Concrete examples of the compounds which prove preferable among the compounds that are usable for this invention are shown in Table 1 and Table 2 below.

TABLE 1

| Compound No. | m | n |
|---|---|---|
| 1 | 3 | 1 |
| 2 | 3 | 2 |
| 3 | 3 | 3 |
| 4 | 4 | 1 |
| 5 | 4 | 2 |
| 6 | 4 | 3 |
| 7 | 5 | 1 |
| 8 | 5 | 2 |
| 9 | 5 | 3 |
| 10 | 2 | 1 |
| 11 | 2 | 2 |
| 12 | 2 | 3 |

TABLE 2

| Compound No. | m | n |
|---|---|---|
| 13 | 3 | 1 |
| 14 | 3 | 2 |
| 15 | 3 | 3 |
| 16 | 4 | 1 |
| 17 | 4 | 2 |
| 18 | 4 | 3 |
| 19 | 5 | 1 |
| 20 | 5 | 2 |
| 21 | 5 | 3 |
| 22 | 2 | 1 |
| 23 | 2 | 2 |
| 24 | 2 | 3 |

As concrete examples of the acids in the acid addition salts of the compounds represented by the formula (I) or racemates thereof, such inorganic acids as hydrochloric acid, hydrobromic acid, sulfuric acid, phosphric acids, as hydrochloric acid and such organic acids as acetic acid, succinic acids, adipic acid, propionic acid, tartaric acid, fumaric acid, maleic acid, oxalic acid, citric acid, benzoic acid, toluene sulfonic acid, and methane sulfonic acid may be cited. Among the acid addition salts enumerated above, it is particularly advantageous to use the hydrochlorides of the compounds mentioned above.

In all the compound mentioned above, Compound No. 1 in Table 1, namely the compound of the formula (II), is most advantageous. The hydrochloric acid addition salt of this compound is occasionally referred to hereinafter as MKC-242.

The alkylene dioxybenzene derivatives of the general formula (I) mention above, racemates thereof, and acid addition salts thereof which are used for this invention are known compounds. They can be easily synthesized by methods which are disclosed in U.S. Pat. No. 4,684,739 and U.S. Pat. No. 5,168,099, for example, and methods which conform thereto with necessary modifications.

The medicine of this invention for oculopathy contains the 5-HT$_{1A}$ ligand mentioned above as an active component thereof and can be formulated in various types such as ingesting agent, injecting agent, eye lotion, and eye ointment. The ingesting agent may be used in such forms as tablets, capsules, powder, solution, and elixir. When it is used in any of these forms, it may incorporate in the composition thereof a solid or liquid pharmaceutical carrier which has no toxicity.

The solid carriers which are usable for the purpose of this incorporation include cellulose, mannitol, lactose, starch, polyvinyl pyrrolidone, starch derivatives such as sodium starch glycolate, and sodium lauryl sulfate, for example. The active component, either alone or in combination with an adjuvant, may be packed in capsules, molded into tablets, or pulverized and wrapped.

These capsules, tablets, and wraps of powder generally contain the active component at a concentration in the range of 5–95% by weight, preferably 25–90% by weight.

In these forms of administration, one dose of medicine can contain the effective component in an amount in the range of 5–500 mg, preferably 5–250 mg.

As liquid carriers, water, petroleum, oils of vegetable origins such as peanut oil, soybean oil, and sesame oil, oils of animal origins, mineral oils, and synthetic oils, for example.

Generally, physiological saline solution, dextrose or similar sucrose solution, and glycols such as propylene glycol and polyethylene glycol are preferable liquid carriers. Particularly, the injecting agent using physiological saline solution is generally so prepared as to contain the effective component in the concentration in the range of 0.5–20% by weight, preferably 1–10% by weight.

Appropriately the medicine for oral administration is a suspension or a syrup containing the active component at a concentration in the range of 0.5–20% by weight. As the carrier in this case, such a water-like excipient as perfume, juice, or pharmaceutical micell is used.

The eye lotion for dropwise application can be prepared by dissolving the 5-HT$_{1A}$ ligand in water and suitably adding the various additives shown below to the aqueous solution.

The buffer solutions which are usable herein include phosphate buffer, borate buffer, citrate buffer, tartrate buffer, acetate buffer, and amino acids, for example. The isotonizers which are usable herein include such saccharides as sorbitol, glucose, mannitol, such polyhydric alcohols as glycerin and propylene glycol, and such salts as sodium chloride, for example. The antiseptics which are usable herein include such quaternary ammonium salts as benzalkonium chloride and benzetonium chloride, paraoxybenzoic esters such as methyl paraoxybenzoate and ethyl paraoxybenzoate, benzyl alcohol, phenetyl alcohol, sorbic acid and salts thereof, thimerosal, and chlorobutanol, for example. The tackifying agents which are usable herein include hydroxy ethyl cellulose, hydroxy propyl cellulose, methyl cellulose, hydroxypropyl methyl cellulose, carboxymethyl cellulose, and salts thereof, for example.

The ointment is prepared by evenly mixing the 5-$HT_{1A}$ ligand mentioned above with such a suitable base as vaseline and, when necessary, adding to the resultant mixture a preserving agent, a stabilizer, or other suitable additives.

Pharmaceutical compositions of other forms can be prepared by pertinent methods which are well known to persons skilled in the art. The forms of medicinal agents as one embodiment of the medicine of this invention are not limited to those described above.

The amount of the 5-$HT_{1A}$ receptor ligand contained in the medicine of this invention for oculopathy to be utilized for therapeutic purpose varies with the age and body weight of the patient, the symptom, and the graveness of disease. It is a matter to be decided by a clinician. Generally, the daily dosage of the 5-$HT_{1A}$ receptor ligand is in the range of 0.001–10.0 mg/kg of body weight. The administration of this medicine, when necessary, is made on two or more days. When the 5-$HT_{1A}$ receptor ligand happens to be an alkylene dioxybenzene derivative of the formula (I) mentioned above, the daily dosage of the medicine containing it is appropriately in the range of 0.05–3 mg/kg of body weight. For oral administration, the medicine is prepared in such a form that the unit content of the alkylene dioxybenzene derivative in the medicine will fall generally in the range of 0.5–500 mg, preferably 1–100 mg. The patient is directed to ingest 5 mg of this medicine at a time, generally 1 to 3 times daily. For administration by injection, the medicine is prepared in the form of a solution such that the unit content of the alkylene dioxybenzene derivative in the medicine will generally fall in the range of 0.5–20% by weight, preferably 1–10% by weight. This solution is injected in a dose in the range of 0.03–3 mg at a time, generally 1 to 4 times daily. For administration by dropwise application to the eye, the medicine is prepared in the form of a solution containing the alkylene dioxybenzene derivative at a concentration in the range of 0.1–1%. This solution is applied to the eye 1 to 4 times daily.

The medicine of this invention for oculopathy can be applied for a wide range of ophthalmological diseases by virtue of the aforementioned action of the 5-$HT_{1A}$ receptor ligand to lower the intraocular pressure. The medicine of this invention which has the 5-$HT_{1A}$ receptor ligand as an active component is useful for the prevention and cure of such oculopathy as glaucoma and intraocular hypertension. Incidentally, glaucoma is known in two types, glaucoma of intraocular hypertension and glaucoma of intraocular hypotension which divulges abnormal glaucomatous optic disc and alteration of visual field in spite of normal intraocular pressure. The medicine of this invention is effective for both forms of glaucoma, particularly for glaucoma of intraocular hypertension.

EXAMPLES

The invention will be described more specifically below with reference to working examples. The following examples ought to be construed as an aid in the specific comprehension of the invention and should not impose any limit on the scope of this invention.

Production Example 1

Synthesis of 5-[3-((2S)-(1,4-benzodioxane-2-ilmethyl) amino)propoxy]-1,3-benzodioxol hydrochloride (hydrochloride of Compound No. 1 of Table 1; MKC-242):

In 100 ml of acetonitrile, 5.86 g of 5-(3-aminopropoxy)-1,3-benzodioxol and 3.20 g of (2R)-2-tosyloxymethyl-1,4-benzodioxane (synthesized in accordance with Journal of Medicinal Chemistry, 20, 880, 1977) were dissolved. The resultant solution and 2.77 ml of triethyl amine added thereto were refluxed and stirred for 12 hours. After the reaction was completed, the reaction solution was combined with water and extracted from chloroform. The extract was washed with water and then dried with anhydrous sodium sulfate. The chloroform layer was concentrated and then refined by silica gel column chromatography (chloroform/methanol) to obtain 2.68 g of 5-[3-((2s)-(1,4-benzodioxane-2-ilmethyl)-amino)propoxy]-1,3-benzodioxol.

This product was dissolved in ethyl acetate and then combined with 26% hydrochloric acid/isopropanol. The crystals which consequently formed in the mixture were separated by filtration to obtain 2.37 g of the compound identified in the caption.

Melting point 212–218° C.; $^1$H-NMR (DMSO-$d_6$) δ 9.16 (2H, m), 6.89 (5H, m), 6.63 (1H, d, J=2.4 Hz), 6.37 (1H, dd, J=7.5, 2.5 Hz), 5.95 (2H, s), 4.65 (1H, m), 4.37 (1H, dd, J=12.5, 2.3 Hz), 4.02 (3H, m), 3.25 (4H, m), 2.10 (2H, m).

The optically active compound obtained as described above and a separately synthesized racemate (obtained by the method disclosed in U.S. Pat. No. 4,684,739 were severally amidated with (S)-methoxytrifluoro methylphenyl acetic acid chloride in pyridine and analyzed by high performance liquid chromatography (column: Waters Novapak C18) and compared for optical purity. Thus, the optically active compound was found to possess optical purity of not less than 99% e.e.

Example 1

Eight male rabbits (species: Nippon Hakushoku) each weighing about 2 kg were placed in a retaining can and tamed for about one hour therein and then put to test. After being tamed, the 8 rabbits were tested for initial intraocular pressure. Then, the aqueous 0.2% MKC-242 solution was dropwise applied to the left eyes of four of the rabbits and a distilled water was similarly applied to the left eyes of the remaining four rabbits at a fixed amount of 50 μl. After the elapse of 0.5, 1, 2, 3, and 4 hours following the dropwise application to the eyes, the rabbits were tested for intraocular pressure by the use of an instrument (produced by Alcon Corp. and marketed under trademark designation of "Applanation Pneumatonograph"). The same test was performed 5 days thereafter. The distilled water was applied to the left eyes of the rabbits to which the aqueous 0.2% MKC-242 solution was applied in the initial test and the aqueous 0.2% MKC-242 solution was similarly applied to the left eyes of the rabbits to which the distilled water was applied in the initial test. The aqueous 0.2% MKC-242 solution was prepared by dissolving the MKC-242 in distilled water in a concentration of 0.2% with the aid of an ultrasonic device and a test tube mixer.

The results are shown in FIG. 1. It is clearly noted from FIG. 1 that in the rabbits (control) subjected to dropwise application of distilled water, the intraocular pressure rose with elapse of time from the initial value of 20.8 mmHg to the ultimate value of 22.8 mmHg after 4 hours following the application. In contrast, in the rabbits subjected to the application of the aqueous 0.2% MKC-242 solution, the intraocular pressure began to fall 30 minutes after the application and reached the minimum value of 18.0 mmHg one to two hours after the application. Thus the aqueous 0.2% MKC-242 solution was found to show an action to lower the intraocular pressure by a margin of 2.8 mmHg (one and two hours after application) relative to the initial value of 20.8 mmHg, or by a maximum margin of 4.9 mmHg (two hours after the application) relative to the intraocular pressure of the rabbits of the control group. The solution was found to show an action to lower the intraocular pressure by a maximum margin of 3.9 mmHg (two hours after the application) relative to the opposite eyes (right eyes) to which no application was made.

Example 2

Eight male rabbits (species: Nippon Hakushoku) each weighing about 3 kg were placed in a retaining can and tamed for about one hour therein and then put to test. After being tamed, the 8 rabbits were tested for initial intraocular pressure. Then, the MKC-242 suspended in 0.5% CMC (carboxymethyl cellulose) was orally administered to four of the rabbits at a dose of 30 mg/5 ml/kg of body weight and the 0.5% CMC was similarly administered to the other four rabbits at a dose of 5ml/kg of body weight. After the elapse of 0.5 hour, one hour each between the first through the seventh hour, and 24 hours following the oral administration, the rabbits were tested for intraocular pressure. The measurement of the intraocular pressure was performed in the same manner as in Example 1. The MKC-242 was suspended in the 0.5% CMC solution in a concentration of 0.6% (30 mg/5 ml) by means of agitation and ultrasonic treatment.

Figure 2:
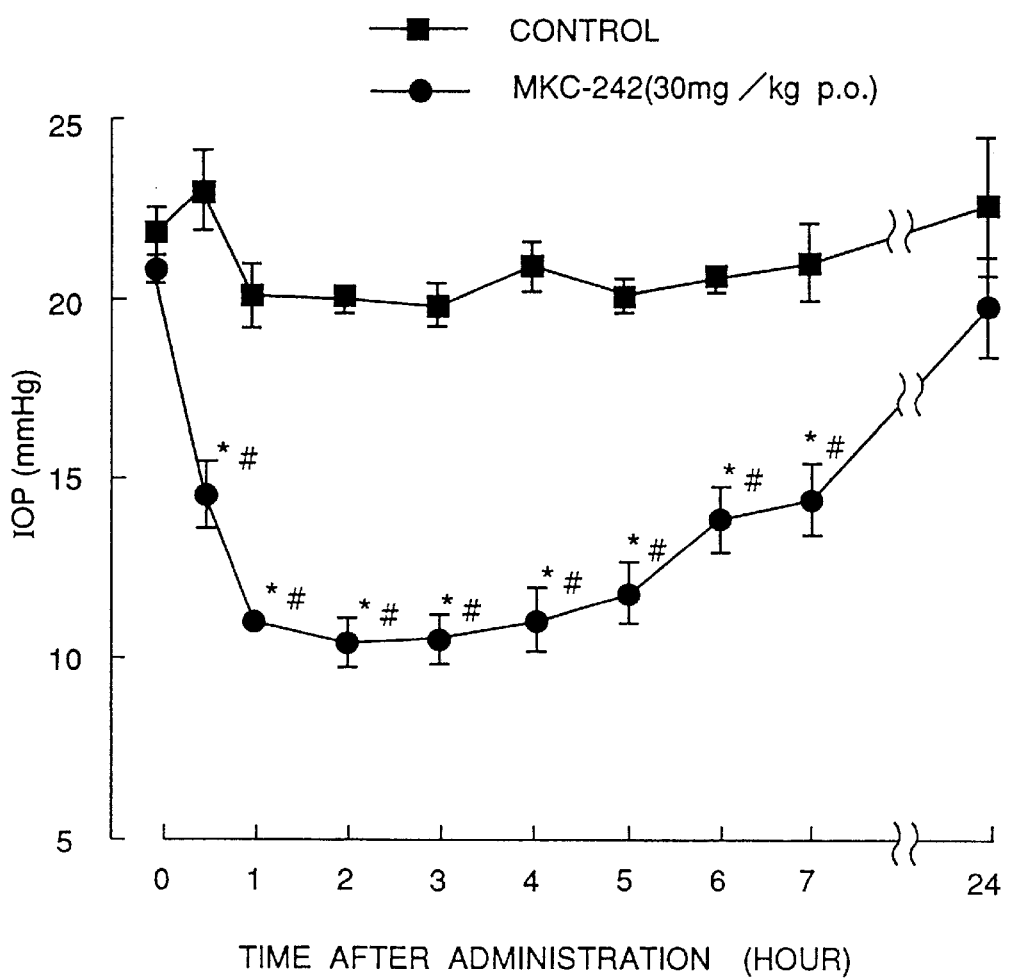
FIG. 2 is a diagram illustrating the action to lower the intraocular pressure manifested by MKC-242 orally administered. In the diagram, the points of measurement and the bars represent the average +/−S.E. of the intraocular pressures in 4 rabbits; # represents the significant difference ($P<0.05$) from the initial intraocular pressure; and * represents the significant difference ($P<0.01$) from the control group.

The results are shown in FIG. 2. It is clearly noted from FIG. 2 that in the rabbits of the control group to which the 0.5% CMC solution was orally administered, the intraocular pressure which had an initial value of 21.9 mmHg was varied in the range of 19.8–23.0 mmHg during the subsequent steps of measurement. In the rabbits to which the MKC-242 was orally administered at a dose of 30 mg/kg, the intraocular pressure began to fall 30 minutes after the oral administration and showed a minimum value of 10.5 mmHg two hours after the administration. Though the intraocular pressure gradually rose after about three hours following the administration, it barely reached 14.3 mmHg seven hours after the administration. This value was low as compared with the initial pressure and the pressure in the rabbits of the control group. The pressure rose and nearly equalled the initial value 24 hours after the administration.

Example 3

Five male rabbits (species: Nippon Hakushoku) each weighing about 2–2.5 kg were placed in a retaining can and tamed for about one hour therein and then put to test. After being tamed, the rabbits were tested for initial intraocular pressure. Then, the aqueous 1% 8-OH-DPAT (produced by Funakoshi K.K.) solution was dropwise applied to one-side eyes of the five rabbits and distilled water was similarly applied to the remaining eyes of the rabbits each in a fixed amount of 50 μl. After the elapse of 0.5, 1, 2, and 3 hours following the dropwise application, the rabbits were tested for intraocular pressure. The measurement of the intraocular pressure was carried out in the same manner as in Example 1.

Figure 3:
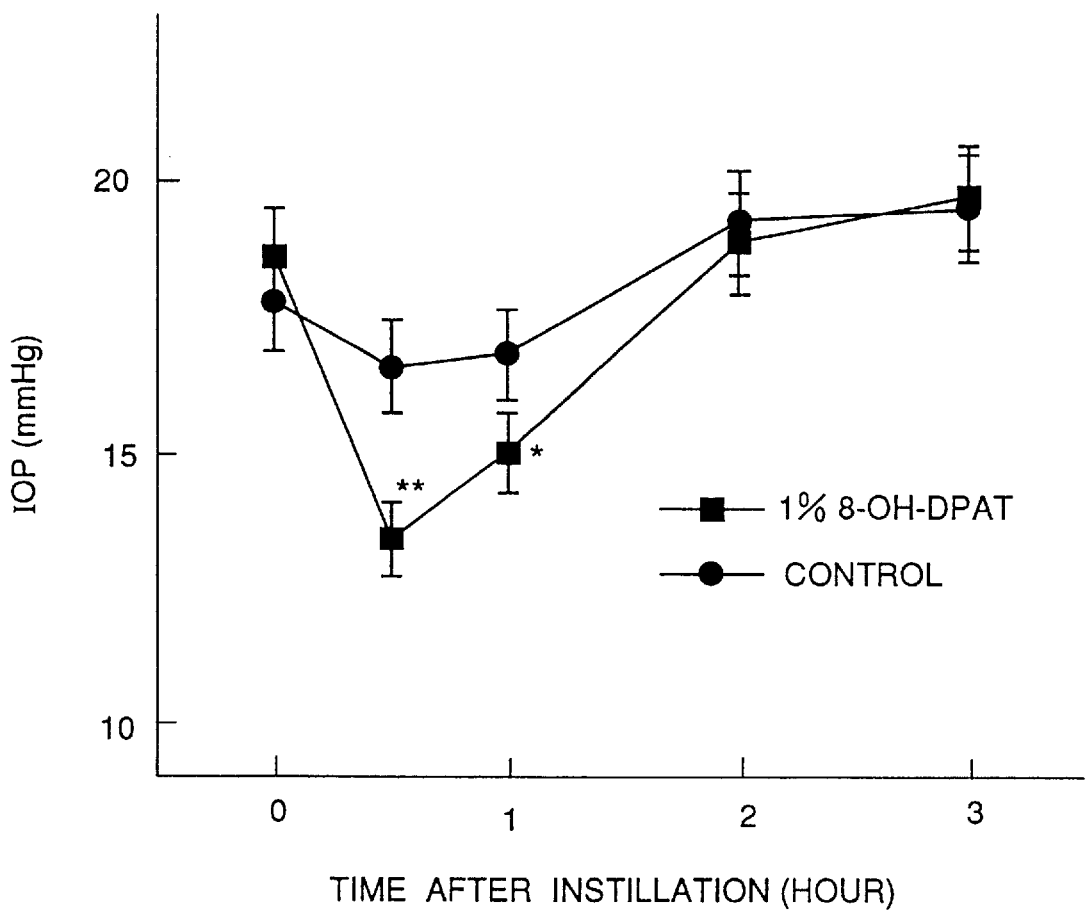
FIG. 3 is a diagram illustrating the action to lower the intraocular pressure manifested by 8-OH-DPAT applied dropwise to the eye. In the diagram, the points of measurement and the bars represent the average +/−S.E. of the intraocular pressures in 5 rabbits and * and ** represent the significant differences ($P<0.05$ and $P<0.01$ respectively) from the initial intraocular pressure.

The results are shown in FIG. 3. It is clearly noted from FIG. 3 that the dropwise application of 8-OH-DPAT at a concentration of 1% brought about a significant decrease of the intraocular pressure of the rabbits.

What is claimed is:

1. A method for the treatment of glaucoma and intraocular hypertension, which comprises administering to a human in need of such treatment a therapeutically effective amount of a compound of the formula (I)

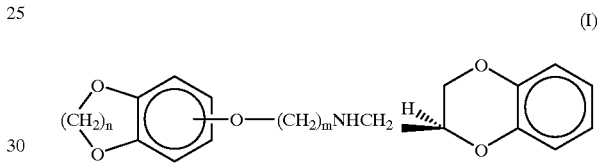

wherein m represents an integer of 2–5 and n represents an integer of 1–3, a racemate thereof, or an acid addition salt thereof.

2. A method according to claim 1, wherein said compound is represented by the formula (II)

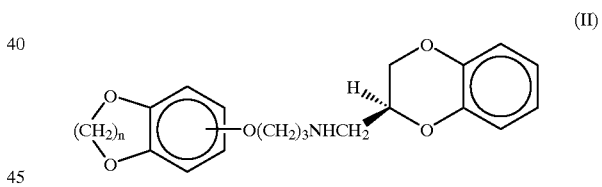

3. A method according to claim 1, for the treatment of glaucoma.

4. A method according to claim 1, for the treatment of intraocular hypertension.

* * * * *